(12) United States Patent
Mohiuddin et al.

(10) Patent No.: US 10,076,355 B2
(45) Date of Patent: Sep. 18, 2018

(54) CIRCUMCISION TOOL

(71) Applicants: Mohammed Muddassir Mohiuddin, Frederick, MD (US); Mohammed Taiyab Mohiuddin, Frederick, MD (US)

(72) Inventors: Mohammed Muddassir Mohiuddin, Frederick, MD (US); Mohammed Taiyab Mohiuddin, Frederick, MD (US)

(*) Notice: Subject to any disclaimer, the term of this patent is extended or adjusted under 35 U.S.C. 154(b) by 0 days.

(21) Appl. No.: 15/651,787

(22) Filed: Jul. 17, 2017

(65) Prior Publication Data
US 2018/0014841 A1   Jan. 18, 2018

Related U.S. Application Data

(60) Provisional application No. 62/362,636, filed on Jul. 15, 2016.

(51) Int. Cl.
*A61B 17/32*   (2006.01)
*A61B 17/326*   (2006.01)
*A61B 17/28*   (2006.01)

(52) U.S. Cl.
CPC .......... *A61B 17/326* (2013.01); *A61B 17/282* (2013.01); *A61B 17/2833* (2013.01); *A61B 2017/2837* (2013.01)

(58) Field of Classification Search
CPC .... A61B 17/2804; A61B 17/28; A61B 17/326
See application file for complete search history.

(56) References Cited

U.S. PATENT DOCUMENTS

| 5,163,943 A | * | 11/1992 | Mohiuddin | .......... A61B 17/326 227/175.1 |
| 2011/0098718 A1 | * | 4/2011 | Shang | .................. A61B 17/326 606/118 |

* cited by examiner

*Primary Examiner* — Kathleen Holwerda
*Assistant Examiner* — Christina Lauer

(57) ABSTRACT

A circumcision tool for securely holding and cutting the prepuce of a penis includes a forceps body and a prepuce clamp. The forceps body includes a first arm and a second arm that are pivotally connected to each other to form a dual-lever body. A first handle is terminally connected to the first arm, while a second handle is terminally connected to the second arm, allowing for manipulation of the first arm and the second arm. The prepuce clamp includes a first hinged clamp and a second hinged clamp; the first hinged clamp being connected to the first arm opposite the first handle and the second hinged clamp being connected to the second arm opposite the second handle. The first hinged clamp and the second hinged clamp are ring shaped members that can be laterally separated to fit around the penis.

18 Claims, 10 Drawing Sheets

CIRCUMCISION TOOL

The current application claims a priority to the U.S. Provisional Patent application Ser. No. 62/362,636 filed on Jul. 15, 2016.

FIELD OF THE INVENTION

The present invention relates generally to medical devices. More specifically, the present invention is a circumcision tool for removing the foreskin from a penis.

BACKGROUND OF THE INVENTION

Male circumcision is a medical procedure that has been performed for thousands of years, for religious purposes as well as for medical benefits. Newborn and adult circumcisions are thought to reduce the risk of several health problems, including urinary tract infections, transmission of sexually transmitted disease, and penile cancer. In addition, the removal of the prepuce, or foreskin, simply makes it easier to wash and clean the penis, which can in turn contribute to positive health changes. For these reasons and more, circumcisions are already quite popular, and continue to gain international popularity.

In order to perform a successful circumcision, a practitioner must have the right equipment on hand. A sterile environment and aseptic tools are essential, as open wounds can lead to infection in unclean conditions. One common method for circumcising a penis is called the plastibell method. The practitioner places a device on the glans of the penis that separates the glans from the foreskin in order to facilitate subsequent cutting. The plastibell is then partially left on the penis to fall off as the skin dies. In order to perform the plastibell method properly, however, a practitioner needs to have an appropriately sized plastibell apparatus on hand. In addition, the device is not reusable, and complications may arise if the remaining plastibell segment becomes stuck. Another common process is the Gomco bell and clamp procedure. This procedure also requires the use of an appropriately-sized apparatus for placement atop the glans of the penis. The Gomco clamp is also a rather large object that may be difficult to hold properly in place. In many other common circumcision procedures in general, the operation involves using two pairs of tweezers to pull the foreskin from the glans, and a surgical knife to perform the cuts. This arrangement is less than optimal, as it requires the use of three hands to perform the surgery, which naturally crowds the surgical area. Particularly in developing countries where resources, including proper equipment and qualified practitioners, are a commodity, there is a distinct lack of a convenient invention or apparatus that allows a practitioner to control the pressure applied to the prepuce with one hand, while leaving the other hand free to operate a surgical knife. What is also needed is a device that can function properly with different glans sizes. Further, a device with all necessary components attached would simplify the circumcision process, making it more intuitive to use.

Therefore, it is an objective of the present invention to provide an apparatus that allows for a practitioner to secure a penis in place during circumcision surgery. The present invention is a scissor-like apparatus that hinges at the tip portion to allow for addition of a glans of any size. Once adjusted accordingly, the present invention clamps down on the prepuce to hold it in position during cutting. Once cutting is complete, the clamp may continue to be held to facilitate recovery by allowing blood to coagulate at the affected area. The present invention allows for a single practitioner to perform a circumcision without necessitating the use of assistants.

DETAIL DESCRIPTIONS OF THE INVENTION

All illustrations of the drawings are for the purpose of describing selected versions of the present invention and are not intended to limit the scope of the present invention.

The present invention is a circumcision tool that is used to remove the foreskin from a penis. The present invention assists a practitioner in performing a circumcision by allowing the practitioner to clamp and cut the foreskin using only one hand. Furthermore, the present invention is adaptable to different penis sizes, thus reducing the number of medical instruments needed by the practitioner.

Figure 1:
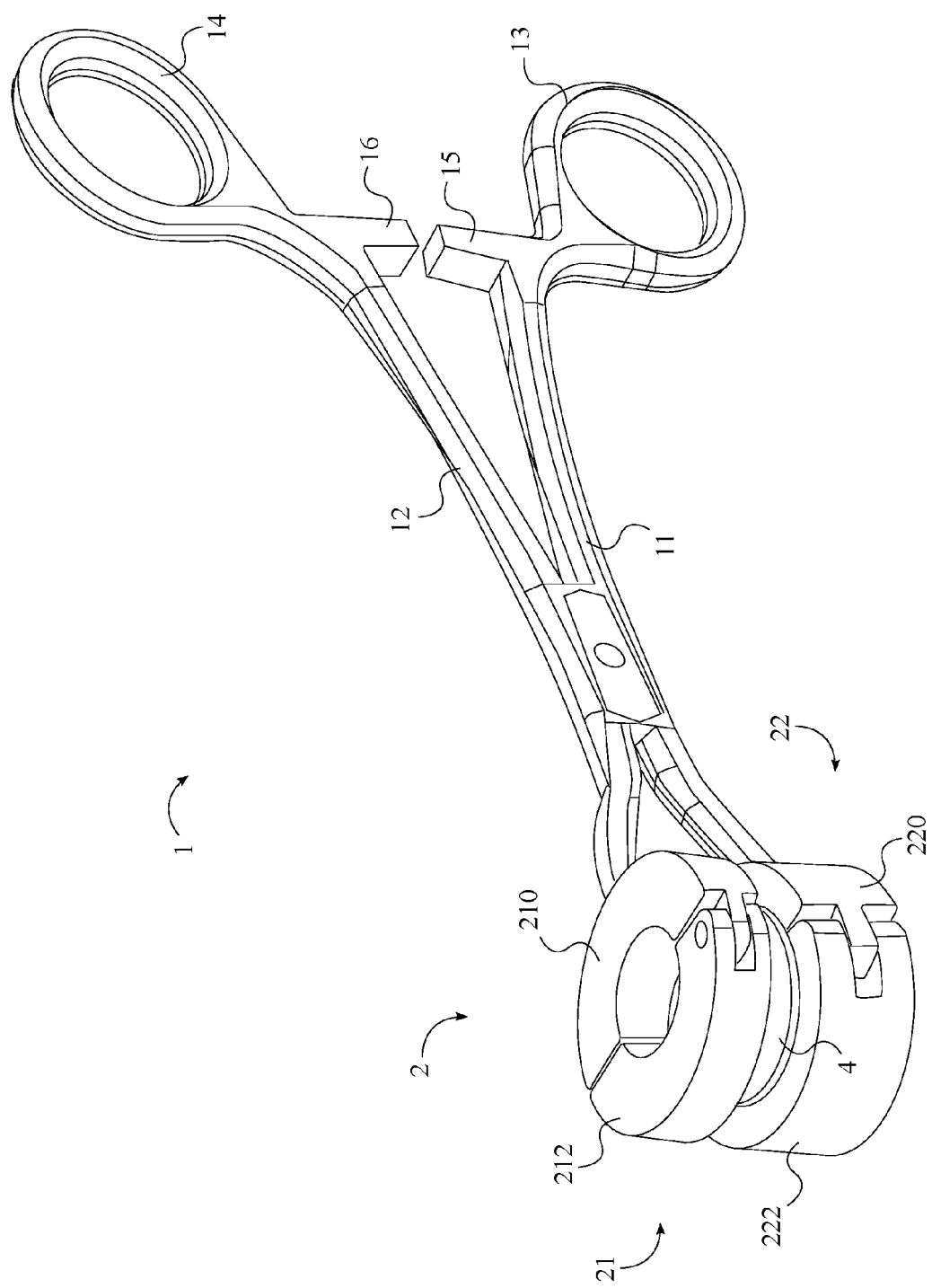
FIG. 1 is a perspective view of the present invention.

In reference to FIG. 1, the present invention comprises a forceps body 1 and a prepuce clamp 2. The prepuce clamp 2 is fitted around the penis, while the forceps body 1 allows the practitioner to manipulate the prepuce clamp 2 in order to cut and remove the foreskin. The forceps body 1 provides a dual-lever body that is used by the practitioner to apply force to two separate members of the prepuce clamp 2 in order to cut the foreskin.

In further reference to FIG. 1, the forceps body 1 comprises a first arm 11, a second arm 12, a first handle 13, and a second handle 14. The first arm 11 and the second arm 12 are each an elongated member that acts as a lever to provide a clamping force for the prepuce clamp 2. The first handle 13 is terminally connected to the first arm 11, and provides the practitioner with a means for grasping and manipulating the first arm 11. Similarly, the second handle 14 is terminally connected to the second arm 12 and provides the practitioner with a means for grasping and manipulating the second arm 12. The first handle 13 and the second handle 14 provide continuous contact with the practitioner's fingers, allowing the practitioner to securely maneuver the forceps body 1.

Figure 2:
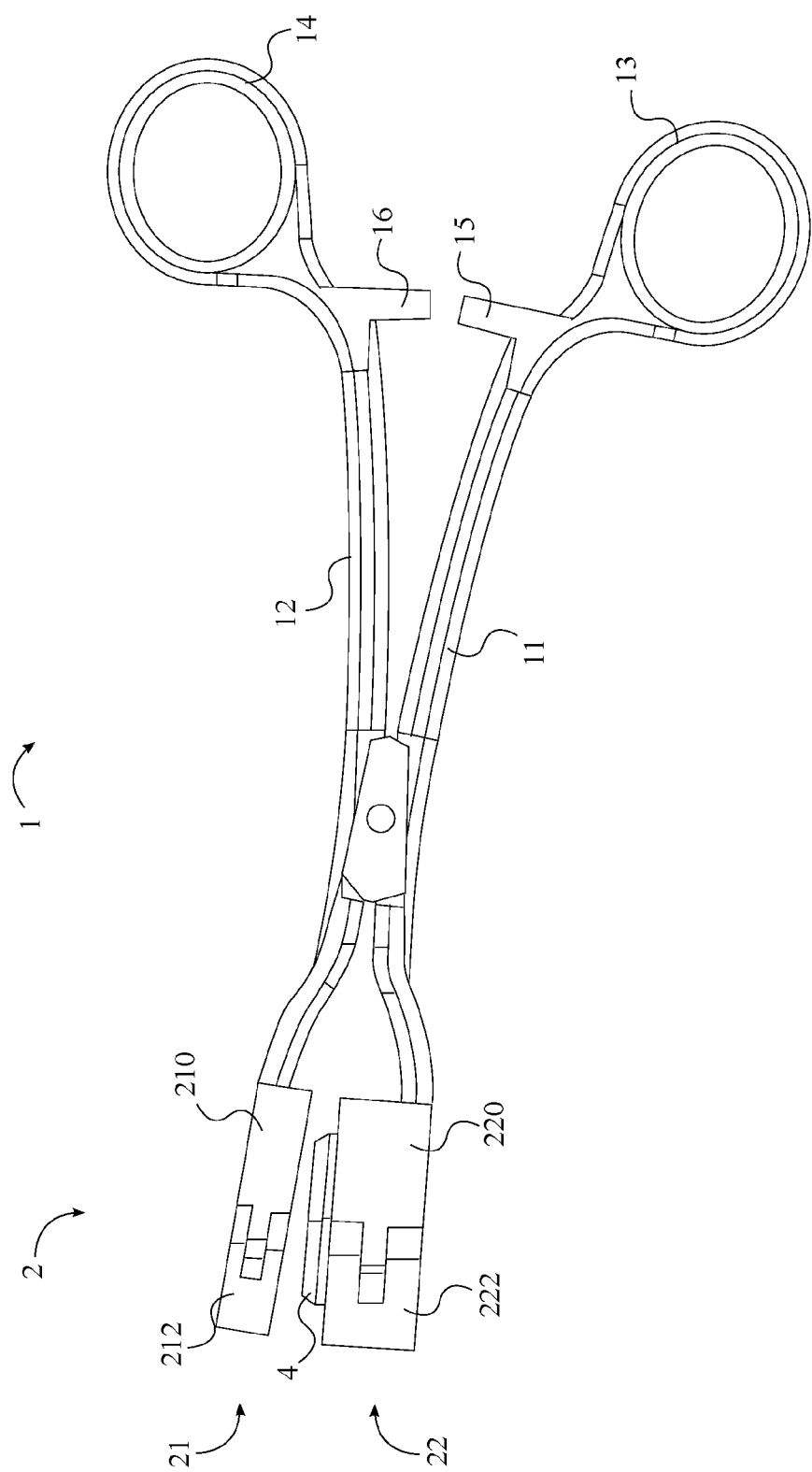
FIG. 2 is a right side elevational view of the present invention.

In reference to FIG. 2, in the preferred embodiment of the present invention, each of the first handle 13 and the second handle 14 is a closed loop. The first handle 13 and the second handle 14 may each form a circular loop, oblong loop, or any other ergonomic shaped profile deemed suitable for comfortably holding and securely manipulating the first arm 11 and the second arm 12. In other embodiments of the present invention, the first handle 13 or the second handle 14 may be an open loop, or a completely other means for engaging with the practitioner's fingers or another mechanical body. For example, the first handle 13 and the second handle 14 can provide a means for interfacing the first arm 11 and the second arm 12, respectively, with mechanical actuators that are controlled remotely by a practitioner.

In reference to FIG. 1, the prepuce clamp 2 comprises a first hinged clamp 21 and a second hinged clamp 22. The first hinged clamp 21 is terminally connected to the first arm 11, wherein the first handle 13 is positioned opposite the first hinged clamp 21, along the first arm 11. Similarly, the second hinged clamp 22 is terminally connected to the second arm 12, wherein the second handle 14 is positioned opposite the second hinged clamp 22, along the second arm 12. The first arm 11 is pivotally connected to the second arm 12, wherein the practitioner can manipulate the distance between the first hinged clamp 21 and second hinged clamp 22 by utilizing the first handle 13 and the second handle 14.

The first arm 11 is pivotally connected to the second arm 12 by a pin. In one embodiment, the pin is terminally connected to the first arm 11, wherein the pin engages with a hole in the second arm 12. In another embodiment, the pin is terminally connected to the second arm 12, wherein the pin engages with a hole in the first arm 11. In yet another embodiment, the pin engages with a hole in both the first arm 11 and the second arm 12, wherein the pin has a first flanged end and a second flanged end that prevent the first arm 11 and the second arm 12 from sliding off of the pin. The pin provides a shaft about which one or both of the first arm 11 and the second arm 12 may rotate.

In the preferred embodiment of the present invention, the pin is positioned approximately at the midpoint of the length of the first arm 11 and the midpoint of the length of the second arm 12. However, in other embodiments of the present invention, the pin may be located off center, closer to either the first handle 13 and the second handle 14, or closer to the prepuce clamp 2. In this way, the torque required to open and close the prepuce clamp 2 can be altered from one embodiment to another.

Figure 3:
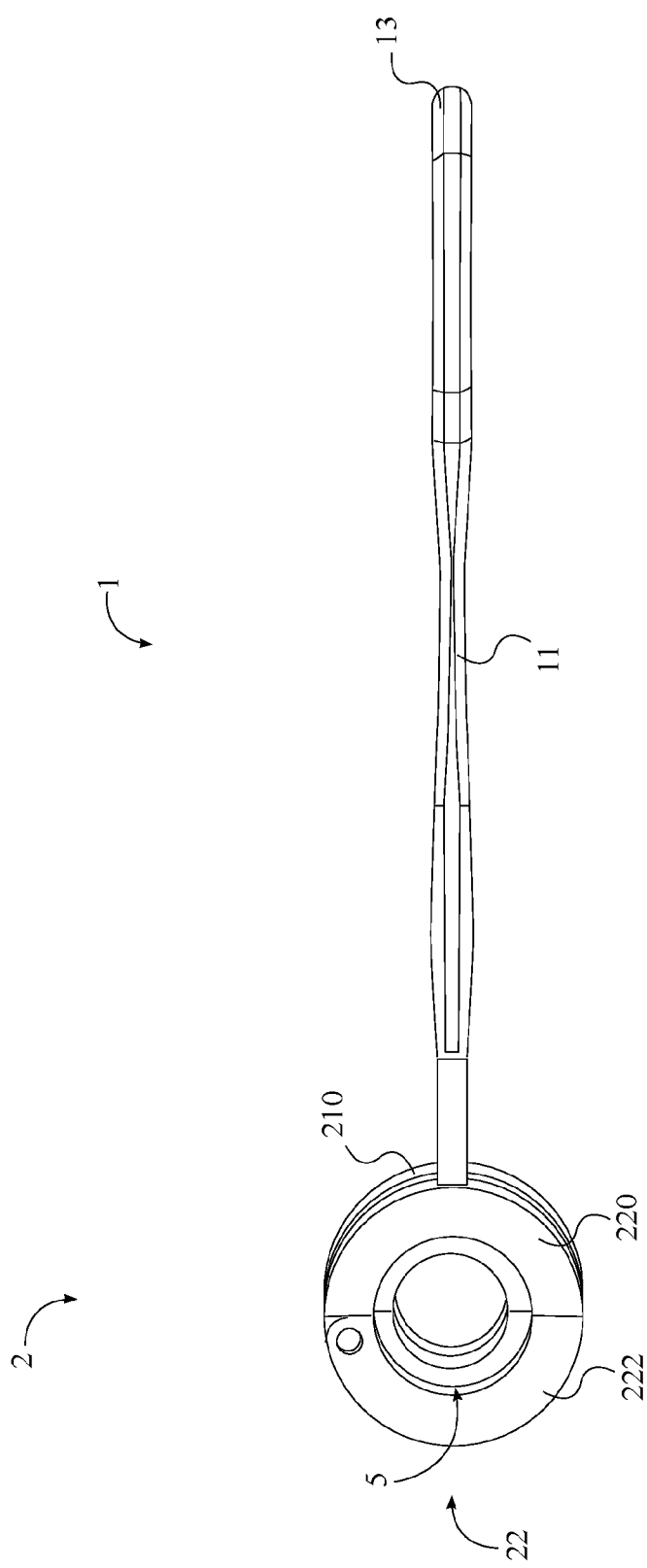
FIG. 3 is a bottom plan view of the present invention.
Figure 4:
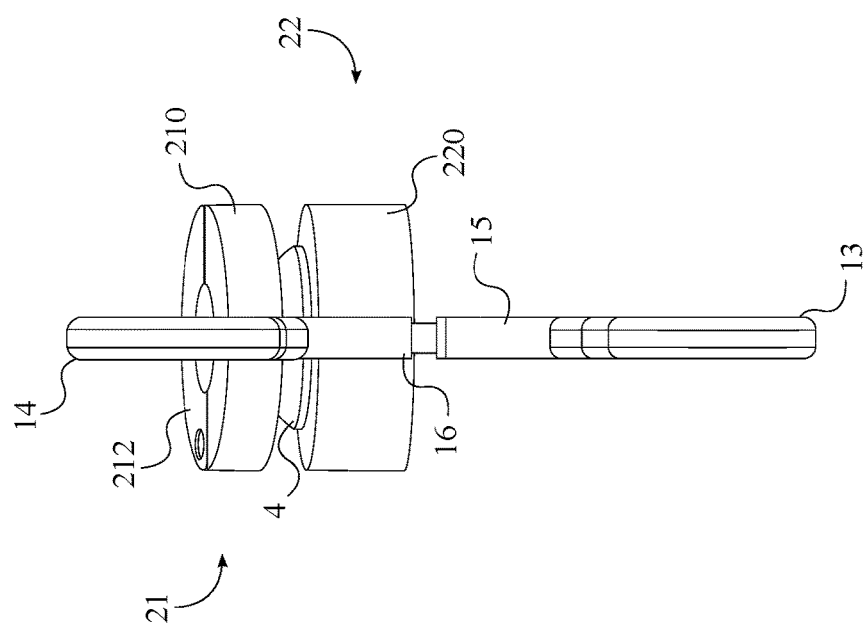
FIG. 4 is a rear elevational view of the present invention.

In reference to FIG. 3, the first hinged clamp 21 and the second hinged clamp 22 are both ring shaped, such that the first hinged clamp 21 and the second hinged clamp 22 completely encircle the penis. Both the first hinged clamp 21 and the second hinged clamp 22 have a means for laterally opening and closing in order to fit the prepuce clamp 2 around the penis. More specifically, the first hinged clamp 21 comprises a first secured section 210 and a first adjustable section 212, while the second hinged clamp 22 comprises a second secured section 220 and a second adjustable section 222.

Figure 7:
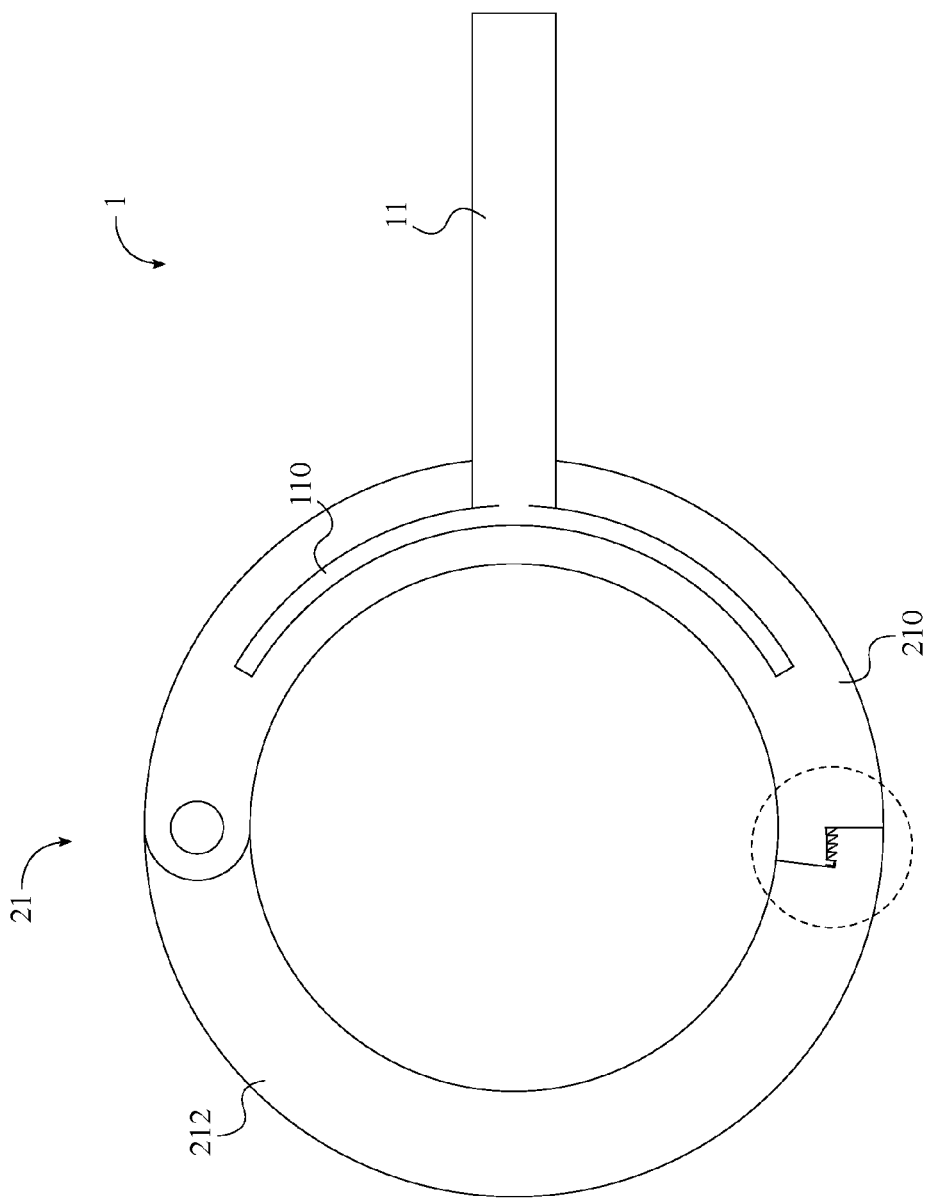
FIG. 7 is a top plan view showing the first pressure distributor slotted into the first hinged clamp.

In reference to FIG. 7, the first secured section 210 and the first adjustable section 212 are both arc shaped members that, when aligned with one another, form the ring shape of the first hinged clamp 21. The first secured section 210 is adjacently connected to the first arm 11, wherein the first secured section 210 is fixed in place. Meanwhile, the first adjustable section 212 is hingedly connected to one end of the first secured section 210. In this way, the first hinged clamp 21 can be opened and closed in order to be fitted around the penis. In one embodiment, the first adjustable section 212 is engaged with the first secured section 210 through a pin, wherein the first adjustable section 212 rotates about the pin.

In further reference to FIG. 7, opposite the hinged connection, the first secured section 210 and the first adjustable section 212 are selectively engaged with one another. The selective engagement between the first adjustable section 212 and the first secured section 210 allows the first hinged clamp 21 to remain in the closed position for the cutting of the foreskin. Once the foreskin has been cut, the first adjustable section 212 can then be released from the first secured section 210 in order to remove the first hinged clamp 21 from the penis.

Figure 8:
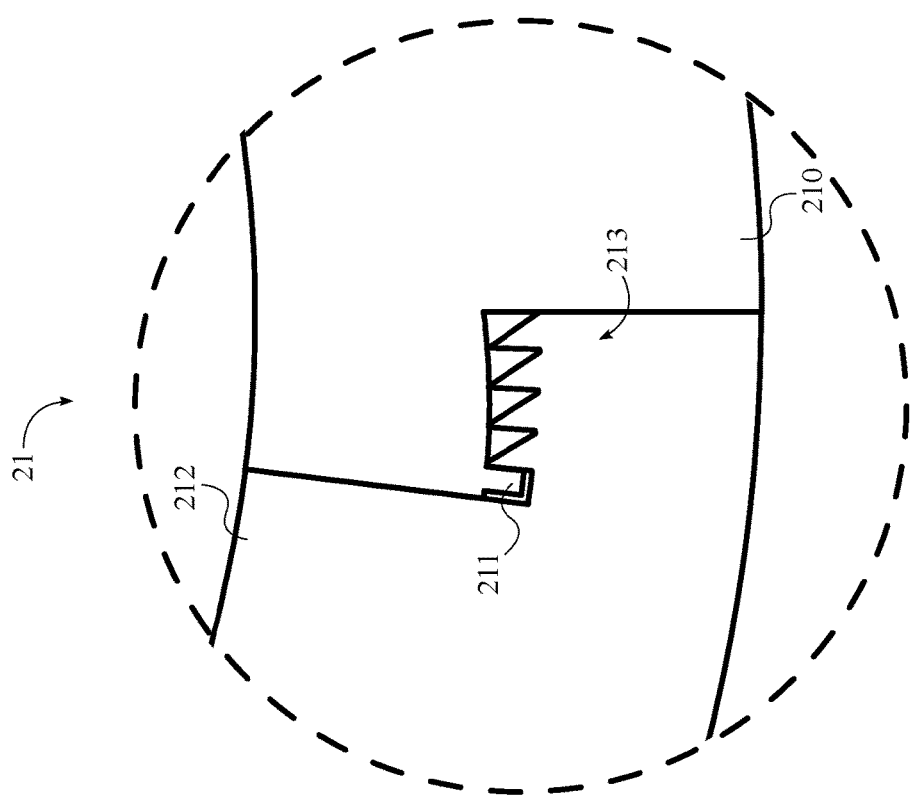
FIG. 8 detail view of the circled region in FIG. 7, showing the first latch engaging with the first keeper.

In reference to FIG. 8, in order to engage the first adjustable section 212 with the first secured section 210, the first adjustable section 212 comprises a first latch 213, while the first secured section 210 comprises a first keeper 211; the first latch 213 being selectively engaged with the first keeper 211. The first latch 213 connects with the first keeper 211 to form a temporary, yet secure, connection between the first adjustable section 212 and the first secured section 210. The first latch 213 and the first keeper 211 also provide a simple means of releasing the first adjustable section 212 from the first secured section 210. In some embodiments, the position of the first latch 213 and the first keeper 211 may be reversed, wherein the first adjustable section 212 comprises the first keeper 211 and the first secured section 210 comprises the first latch 213.

In some embodiments, the first latch 213 is a linear ratchet having one or more teeth, while the first keeper 211 is either a tooth or a cavity. The first latch 213 slides over top of the first secured section 210, wherein the one or more teeth engages with the first keeper 211. The one or more teeth allow the first latch 213 to slide in one direction, further tightening the first hinged clamp 21 in the closed position. To release the first latch 213 from the first keeper 211, the first latch 213 can be lifted away from the first keeper 211, or otherwise displaced such that the one or more teeth is no longer engaged with the first keeper 211.

Figure 9:
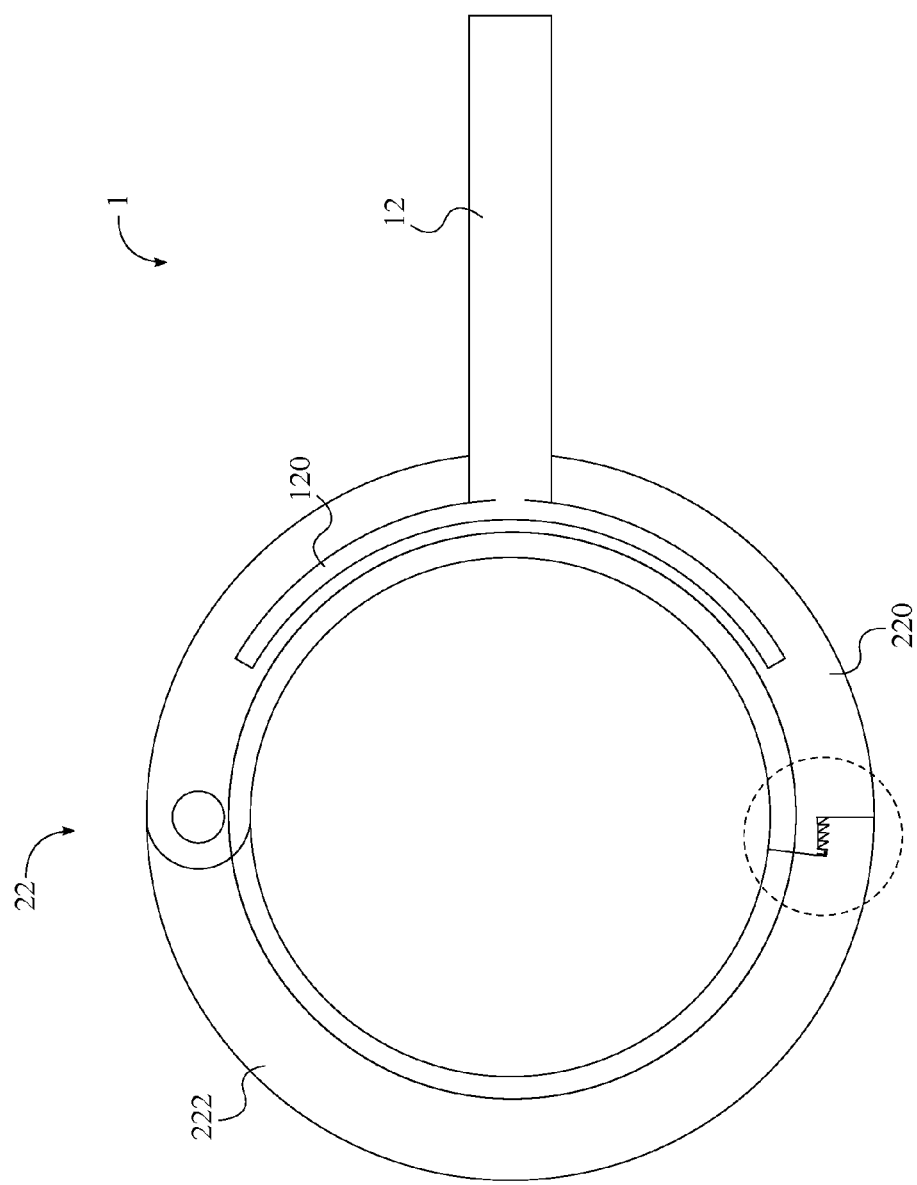
FIG. 9 is a top plan view showing the second pressure distributor slotted into the second hinged clamp.

In reference to FIG. 9, similar to the two sections of the first hinged clamp 21, the second secured section 220 and the second adjustable section 222 are both arc shaped members that, when aligned with one another, form the ring shape of the second hinged clamp 22. The second secured section 220 is adjacently connected to the second arm 12, wherein the second secured section 220 is fixed in place. Meanwhile, the second adjustable section 222 is hingedly connected to one end of the second secured section 220. In this way, the second hinged clamp 22 can be opened and closed in order to be fitted around the penis. In one embodiment, the second adjustable section 222 is engaged with the second secured section 220 through a pin, wherein the second adjustable section 222 rotates about the pin.

In further reference to FIG. 9, opposite the hinged connection, the second secured section 220 and the second adjustable section 222 are selectively engaged with one another. The selective engagement between the second adjustable section 222 and the second secured section 220 allows the second hinged clamp 22 to remain in the closed position for the cutting of the foreskin. Once the foreskin has been cut, the second adjustable section 222 can then be released from the second secured section 220 in order to remove the second hinged clamp 22 from the penis.

Figure 10:
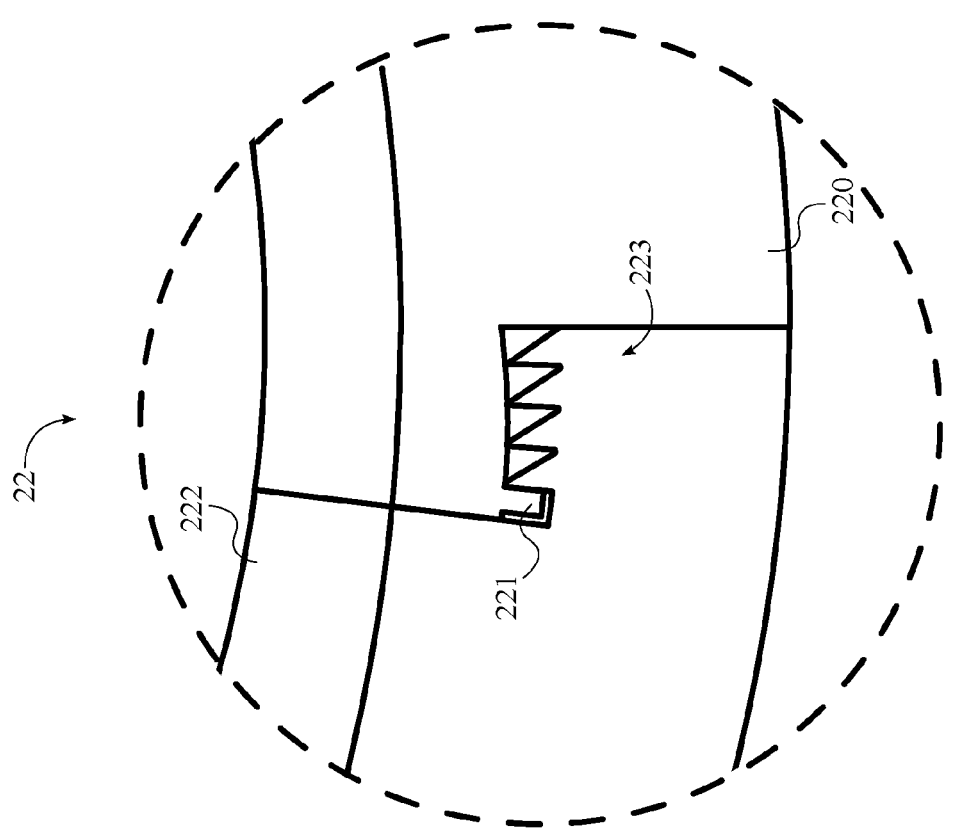
FIG. 10 detail view of the circled region in FIG. 9, showing the second latch engaging with the second keeper.

In reference to FIG. 10, in order to engage the second adjustable section 222 with the second secured section 220, the second adjustable section 222 comprises a second latch 223, while the second secured section 220 comprises a second keeper 221; the second latch 223 being selectively engaged with the second keeper 221. The second latch 223 connects with the second keeper 221 to form a temporary, yet secure, connection between the second adjustable section 222 and the second secured section 220. The second latch 223 and the second keeper 221 also provide a simple means of releasing the second adjustable section 222 from the second secured section 220. In some embodiments, the position of the second latch 223 and the second keeper 221 may be reversed, wherein the second adjustable section 222 comprises the second keeper 221 and the second secured section 220 comprises the second latch 223.

In some embodiments, the second latch 223 is a linear ratchet having one or more teeth, while the second keeper 221 is either a tooth or a cavity. The second latch 223 slides over top of the second secured section 220, wherein the one or more teeth engages with the second keeper 221. The one or more teeth allow the second latch 223 to slide in one direction, further tightening the second hinged clamp 22 in the closed position. To release the second latch 223 from the second keeper 221, the second latch 223 can be lifted away from the second keeper 221, or otherwise displaced such that the one or more teeth is no longer engaged with the second keeper 221.

Figure 5:
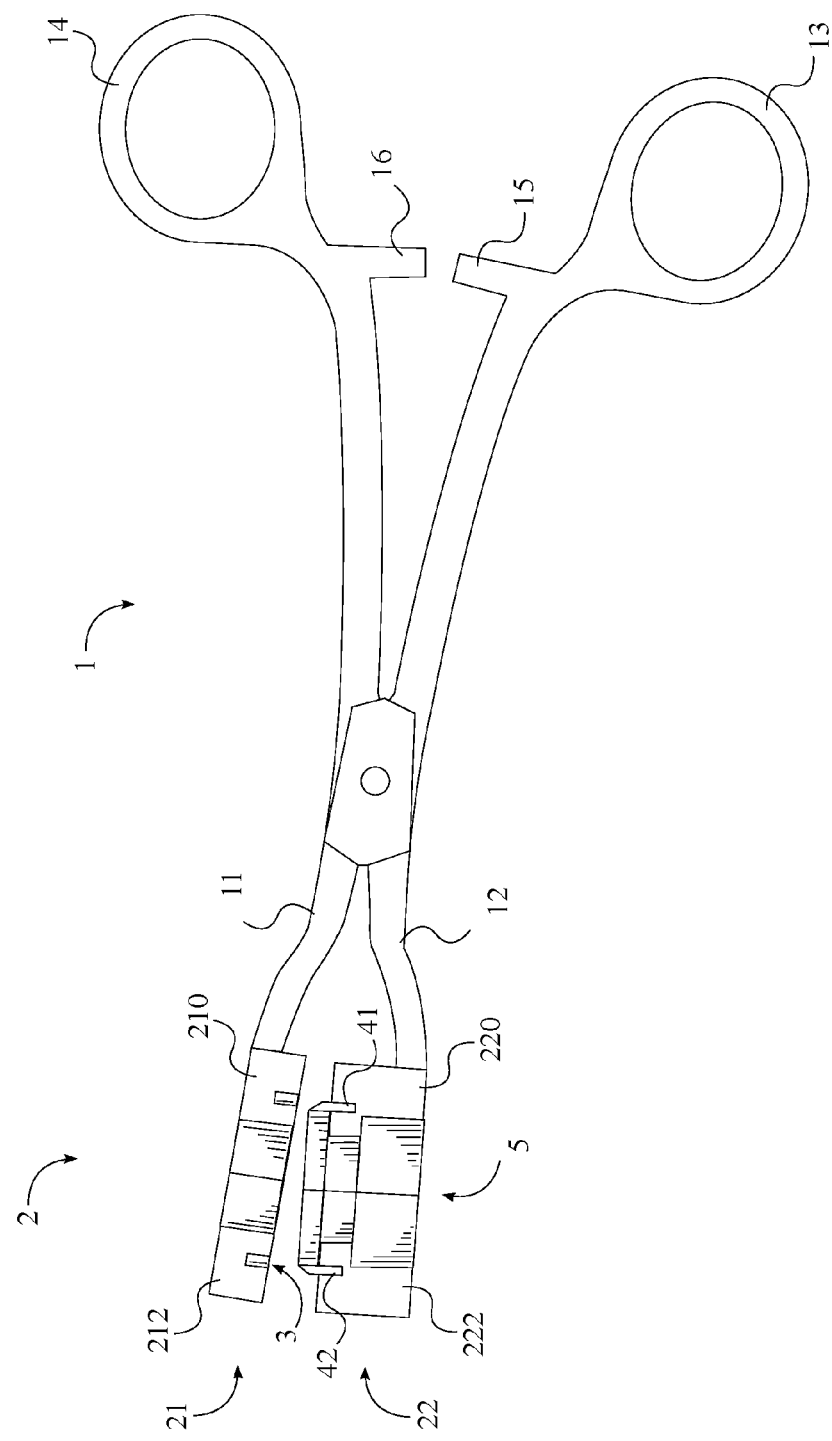
FIG. 5 is a cross-sectional view of the present invention.

In reference to FIG. 5, the prepuce clamp 2 further comprises a channel 3 and a ridge 4. The channel 3 is a curved cut that traverses into the first hinged clamp 21. More specifically, the channel 3 traverses into both the first secured section 210 and the first adjustable section 212. Meanwhile, the ridge 4 is adjacently connected to the second hinged clam, wherein the ridge 4 extends away from the second hinged clamp 22, towards the first hinged clamp 21. The channel 3 is open towards the second hinged clamp 22 in order to receive the ridge 4, when the first hinged clamp 21 and the second hinged clamp 22 are pressed together through manipulation of the first arm 11 and the second arm 12.

In one embodiment, the ridge 4 is secured within a cavity of the second hinged clamp 22. The cavity, much like the channel 3, is a curved cut that traverses into the second hinged clamp 22 and is open towards the first hinged clamp 21. The ridge 4 is positioned into the cavity and secured in place, wherein the ridge 4 then extends outwards from the cavity in order to engage with the channel 3.

In one embodiment, the ridge 4 comprises a first ridge section 41 and a second ridge section 42, as shown in FIG. 5. The first ridge section 41 is connected to the second secured section 220, while the second ridge section 42 is connected to the second adjustable section 222. In this way, the ridge 4 does not impede the rotation of the second adjustable section 222 about the second secured section 220. In another embodiment, the ridge 4 may be a single, flexible piece that is able to bend as the second adjustable section 222 is rotated about the second secured section 220.

In the preferred embodiment of the present invention, the ridge 4 is a cutting blade, wherein the ridge 4 is tapered away from the second hinged clamp 22. When the first hinged clamp 21 and the second hinged clamp 22 have been secured around the penis, the foreskin is folded over the ridge 4. The first hinged clamp 21 is the directed towards the second hinged clamp 22 via the first arm 11 and the second arm 12. As the first hinged clamp 21 engages the second hinged clamp 22, the ridge 4 traverses into the channel 3. As more pressure is applied, the foreskin is clamped between the ridge 4 and the wall of the channel 3, wherein the sharp edge of the ridge 4 cuts through the foreskin.

Figure 6:
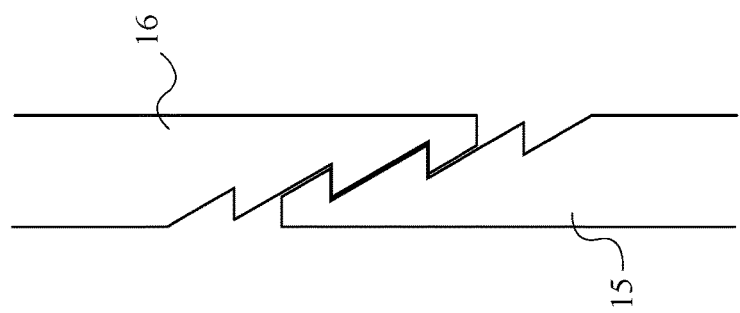
FIG. 6 is a detail view of the first guard interlocking with the second guard.

In reference to FIG. 6 and FIG. 8, in some embodiments of the present invention, the first arm 11 comprises a first pressure distributor 110, while the second arm 12 comprises a second pressure distributor 120. The first pressure distributor 110 is terminally positioned opposite the first handle 13, while the second pressure distributor 120 is terminally positioned opposite the second handle 14. The first pressure distributor 110 and the second pressure distributor 120 extend laterally from the first arm 11 and the second arm 12 respectively. Additionally, the first pressure distributor 110 is curved to match the first hinged clamp 21 and the second pressure distributor 120 is curved to match the second hinged clamp 22.

The first pressure distributor 110 is slotted into the first hinged clamp 21; more specifically, the first pressure distributor 110 is slotted into the first secured section 210, as shown in FIG. 6. Meanwhile, the second pressure distributor 120 is slotted into the second hinged clamp 22; more specifically, the second pressure distributor 120 is slotted into the second secured section 220, as shown in FIG. 8. The first pressure distributor 110 and the second pressure distributor 120 allow force to be more evenly applied to the first hinged clamp 21 and the second hinged clamp 22, when the first hinged clamp 21 and the second hinged clamp 22 are brought together via the first arm 11 and the second arm 12. The pressure distribution allows the prepuce clamp 2 to more securely clamp the foreskin when performing the circumcision.

Furthermore, the first pressure distributor 110 and the second pressure distributor 120 may allow the first hinged clamp 21 and the second hinged clamp 22 to be removed and replaced in some embodiments. In this way, the forceps body 1 can be used with clamps of a different size. In other embodiments, the first hinged clamp 21 and the second hinged clamp 22 may be permanently affixed to the first pressure distributor 110 and the second pressure distributor 120 respectively. In yet other embodiments, the forceps body 1 and the prepuce clamp 2 may be formed from a single molded piece, which is ideal for disposable variants of the present invention.

In reference to FIG. 1-2, the forceps body 1 further comprises a first guard 15 and a second guard 16. The first guard 15 is adjacently connected to the first arm 11, while the second guard 16 is adjacently connected to the second arm 12. In the preferred embodiment of the present invention, the first guard 15 is positioned adjacent to the first handle 13 and the second guard 16 is positioned adjacent to the second handle 14. The first guard 15 is aligned with the second guard 16, wherein the first guard 15 selectively engages the second guard 16 as the first handle 13 is directed towards the second handle 14.

In reference to FIG. 6, in one embodiment, both the first guard 15 and the second guard 16 is a ratchet having one or more teeth. When the first handle 13 is directed towards the second handle 14, the first guard 15 engages the second guard 16. More specifically, the one or more teeth of the first guard 15 engages the one or more teeth of the second guard 16, wherein the first guard 15 and the second guard 16 slide together and interlock. In order to unlock the first guard 15 and the second guard 16, either one or both of the first guard 15 and the second guard 16 is laterally displaced, wherein the one or more teeth of the first guard 15 disengages the one or more teeth of the second guard 16, allowing the first handle 13 to be directed away from the second handle 14. The ratcheting feature of the first guard 15 and the second guard 16 allows the practitioner to leave the first hinged clamp 21 and the second hinged clamp 22 pressed together for an extended period of time, without the practitioner having to maintain force on the first handle 13 and the second handle 14.

In reference to FIG. 1-2, in another embodiment, the first guard 15 and the second guard 16 protect the present invention from mechanical failure due to the application of a high force from the practitioner. Both the first guard 15 and the second guard 16 provide a flat surface that is extended away from the first arm 11 and the second arm 12 respectively. When the first handle 13 is directed towards the second handle 14, the flat surface of the first guard 15 contacts the flat surface of the second guard 16, preventing any further motion of the first handle 13 towards the second handle 14. In this way, the first guard 15 and the second guard 16 prevent excessive force from being applied to the present invention.

In reference to FIG. 5, the prepuce clamp 2 further comprises a glans cavity, wherein the glans cavity traverses into the second hinged clamp 22 opposite the ridge 4. The glans cavity provides an opening in the second hinged clamp 22 with an increased diameter from the main opening of the second hinged clamp 22; the main opening having a diameter equal to the diameter of the opening of the first hinged clamp 21. The glans cavity is intended to receive the head of the penis, and thus the increased diameter of the glans cavity provides a more ergonomic fit around the penis. Additionally, the decrease in diameter from the glans cavity to the main opening of the second hinged clamp 22 prevents the head of the penis from accidentally slipping out of the second hinged clamp 22.

The present invention allows a practitioner to perform a circumcision without outside assistance. To use the present invention, the practitioner places a first finger or thumb through the first handle 13, and places a second finger or thumb of the same hand through the second handle 14; the prepuce clamp 2 being distally positioned from the practitioner's hand. The practitioner can then control the distance of the first hinged clamp 21 from the second hinged clamp 22 by moving the first finger towards or away from the second finger. As the practitioner moves the first finger away from the second finger, the first hinged clamp 21 moves away from the second hinged clamp 22. Alternatively, as the practitioner moves the first finger towards the second finger, the first hinged clamp 21 moves towards the second hinged clamp 22, until the surface of the first hinged clamp 21 meets the surface of the second hinged clamp 22, or until the first guard 15 contacts the second guard 16.

The first hinged clamp 21 and the second hinged clamp 22 are opened by tangentially pulling on the first latch 213 and the second latch 223 respectively, until the force is enough to disengage the first latch 213 from the first keeper 211 and the second latch 223 from the second keeper 221. The first hinged clamp 21 and the second hinged clamp 22 can be opened before or after the practitioner has engaged the first handle 13 and the second handle 14. With the practitioner engaged and both the first hinged clamp 21 and the second hinged clamp 22 open, the prepuce clamp 2 is then fitted around the penis. The first hinged clamp 21 and the second hinged clamp 22 are then closed in order to secure the prepuce clamp 2 around the penis, while the prepuce is folded over the ridge 4. In one embodiment, the prepuce is first cut axially and then folded over the ridge 4.

The practitioner then applies force to the first handle 13 and the second handle 14, bringing the first handle 13 and the second handle 14 closer together, and simultaneously closing the first hinged clamp 21 and the second hinged clamp 22 on the prepuce. In embodiments where the ridge 4 is a cutting blade, the ridge 4 then cuts the prepuce. In other embodiments, the prepuce is clamped in place, allowing the practitioner to cut around the prepuce, removing the prepuce entirely. The practitioner may perform the cut on the inside or on the outside of the ridge 4. The ridge 4, along with the first hinged clamp 21 and the second hinged clamp 22, then hold the wound together, helping the recovery process for the patient. After sufficient time, or post-cutting steps such as cleaning or stitching, the prepuce clamp 2 is released and cleaned to prepare the present invention for subsequent use.

Although the invention has been explained in relation to its preferred embodiment, it is to be understood that many other possible modifications and variations can be made without departing from the spirit and scope of the invention as hereinafter claimed.

What is claimed is:

1. A circumcision tool comprises:
a forceps body;
a prepuce clamp;
the forceps body comprising a first arm, a second arm, a first handle, and a second handle;
the prepuce clamp comprising a first hinged clamp, a second hinged clamp, a channel, a ridge, and a glans cavity;
the first handle and the first hinged clamp being terminally connected to the first arm;
the first handle being positioned opposite the first hinged clamp, along the first arm;
the second handle and the second hinged clamp being terminally connected to the second arm;
the second handle being positioned opposite the second hinged clamp, along the second arm;
the first arm being pivotally connected to the second arm;
the channel traversing into the first hinged clamp;
the ridge being adjacently connected to the second hinged clamp;
the second hinged clamp selectively engaging the channel;
the glans cavity being formed into the second hinged clamp, opposite the ridge;
the first arm comprising a first pressure distributor;
the first pressure distributor being terminally positioned, opposite the first handle; and
the first pressure distributor being slotted into the first hinged clamp.

2. The circumcision tool as claimed in claim 1 comprises:
the forceps body further comprising a first guard and a second guard;
the first guard being adjacently connected to the first arm; and
the second guard being adjacently connected to the second arm.

3. The circumcision tool as claimed in claim 2 comprises:
the first guard being positioned adjacent to the first handle; and
the second guard being positioned adjacent to the second handle.

4. The circumcision tool as claimed in claim 2 comprises:
the first guard selectively engaging the second guard.

5. The circumcision tool as claimed in claim 2 comprises:
the first guard and the second guard each being a ratchet.

6. The circumcision tool as claimed in claim 1 comprises:
the second arm comprising a second pressure distributor;
the second pressure distributor being terminally positioned, opposite the second handle; and
the second pressure distributor being slotted into the second hinged clamp.

7. The circumcision tool as claimed in claim 1, wherein the forceps body and the prepuce clamp are formed as a single molded piece.

8. The circumcision tool as claimed in claim 1 comprises:
the first hinged clamp comprising a first secured section and a first adjustable section;
the first secured section being adjacently connected to the first arm; and
the first adjustable section being hingedly connected to the first secured section.

9. The circumcision tool as claimed in claim 8 comprises:
the first secured section being selectively engaged with the first adjustable section.

10. The circumcision tool as claimed in claim 8 comprises:
the first secured section comprising a first keeper;
the first adjustable section comprising a first latch; and
the first latch being selectively engaged with the first keeper.

11. The circumcision tool as claimed in claim 10, wherein the first latch is a ratchet.

12. The circumcision tool as claimed in claim 1 comprises:
the second hinged clamp comprising a second secured section and a second adjustable section;
the second secured section being adjacently connected to the second arm; and
the second adjustable section being hingedly connected to the second secured section.

13. The circumcision tool as claimed in claim 12 comprises:
the second secured section being selectively engaged with the second adjustable section.

14. The circumcision tool as claimed in claim 12 comprises:
the second secured section comprising a second keeper;
the second adjustable section comprising a second latch; and
the second latch being selectively engaged with the second keeper.

15. The circumcision tool as claimed in claim 14, wherein the second latch is a ratchet.

16. The circumcision tool as claimed in claim 12 comprises:
the ridge comprising a first ridge section and a second ridge section;
the first ridge section being connected to the second secured section; and
the second ridge section being connected to the second adjustable section.

17. The circumcision tool as claimed in claim 1 comprises:
the ridge tapering away from the second hinged clamp.

18. The circumcision tool as claimed in claim 1, wherein the first hinged clamp and the second hinged clamp are ring shaped.

* * * * *